United States Patent [19]

Urbahns et al.

[11] Patent Number: 5,760,073
[45] Date of Patent: Jun. 2, 1998

[54] SUBSTITUTED 4H-PYRANS

[75] Inventors: Klaus Urbahns, Wuppertal; Hans-Georg Heine, Krefeld; Bodo Junge, Wuppertal; Frank Mauler, Overrath; Thomas Glaser, Overrath; Reilinde Wittka, Köln; Jean-Marie-Viktor De Vry, Rösrath, all of Germany

[73] Assignee: Bayer Aktiengesellschaft, Leverkusen, Germany

[21] Appl. No.: 692,964

[22] Filed: Aug. 7, 1996

[30] Foreign Application Priority Data

Aug. 14, 1995 [DE] Germany ............... 195 29 858.6

[51] Int. Cl.$^6$ ............... A61K 31/35; C07D 315/00
[52] U.S. Cl. ............... 514/451; 514/459; 514/460; 549/425; 549/426; 549/427; 549/428
[58] Field of Search ............... 549/425, 426, 549/427, 428; 514/451, 459, 460

[56] References Cited

U.S. PATENT DOCUMENTS 4,622,332  11/1986  Wehinger et al. ............... 514/356

FOREIGN PATENT DOCUMENTS 0088276  9/1983  European Pat. Off. .

OTHER PUBLICATIONS

J. Wolinsky et al., J. Org. Chem, vol. 34, No. 10, pp. 3169–3174 (1969).

P.W.L. Tas, et al., Neurosci. Lett., vol. 94, pp. 279–284 (1988).

*Primary Examiner*—Ba K. Trinh
*Attorney, Agent, or Firm*—Sprung Kramer Schaefer & Briscoe

[57] ABSTRACT

The substituted 4H-pyrans are prepared by reacting either aldehydes or ylidene compounds with suitably substituted β-diketones. The substituted 4H-pyrans according to the invention are suitable as active compounds in medicaments, in particular for the treatment of disorders of the central nervous system.

14 Claims, No Drawings

SUBSTITUTED 4H-PYRANS

The present invention relates to substituted 4H-pyrans, to processes for their preparation and to their use as medicaments, especially as cerebrally active agents.

The publication J. Org. Chem. (1969), 34 (10), 3169–74 discloses some substituted 4H-pyrans.

The present invention now relates to substituted 4H-pyrans of the general formula (I)

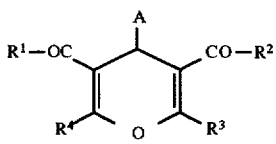

in which

A represents cycloalkyl having 3 to 6 carbon atoms or represents straight-chain or branched alkyl having up to 8 carbon atoms, or represents aryl having 6 to 10 carbon atoms or represents pyridyl, which are optionally substituted up to 3 times by identical or different substituents consisting of nitro, hydroxyl, carboxyl, cyano, aryl having 6 to 10 carbon atoms, halogen, cycloalkyl having 3 to 6 carbon atoms, trifluoromethyl or by straight-chain or branched alkyl, alkoxycarbonyl, alkylthio or alkoxy having in each case up to 6 carbon atoms, or by a group of the formula —O—CO—$R^5$, in which $R^5$ denotes straight-chain or branched alkyl having up to 6 carbon atoms, $R^1$ and $R^2$ are identical or different and represent hydrogen, amino or represent straight-chain or branched alkyl, alkoxy or alkylamino having in each case up to 8 carbon atoms, $R^3$ and $R^4$ are identical or different and represent straight-chain or branched alkyl or acyl having in each case up to 6 carbon atoms, and salts thereof, with the exception of 3,5-diacetyl-2,4,6-trimethyl-4H-pyran, 3,5-diethoxycarbonyl-2,6-dimethyl-4-phenyl-4H-pyran and 3,5-diethoxycarbonyl-2,4,6-trimethyl-4H-pyran.

Within the scope of the invention, physiologically acceptable salts are preferred. Physiologically acceptable salts are, in general, salts of the compounds according to the invention with inorganic or organic acids. Preferred salts are those with inorganic acids, for example hydrochloric acid, hydrobromic acid, phosphoric acid or sulphuric acid, or salts with organic carboxylic or sulphonic acids, for example acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

The compounds according to the invention can exist in stereoisomeric forms whose relationship to one another is either that of image to mirror image (enantiomers) or not (diastereomers). The invention relates both to the isomers and the racemic forms, and also to the diastereomer mixtures. Like these diastereomers, the racemic forms can also be resolved into the stereoisomerically uniform constituents in a known manner.

Preference is given to compounds of the general formula (I) in which

A represents cyclopropyl, cyclobutyl, cyclopentyl or cyclohexyl, or represents straight-chain or branched alkyl having up to 6 carbon atoms, or represents phenyl, naphthyl or pyridyl which are optionally substituted up to 3 times by identical or different substituents consisting of nitro, cyano, fluoro, chloro, bromo, iodo, phenyl, naphthyl, trifluoromethyl, hydroxyl, carboxyl, cyclopropyl, cyclopentyl, cyclohexyl or by straight-chain or branched alkyl, alkoxycarbonyl, alkylthio or alkoxy having in each case up to 4 carbon atoms, or by a group of the formula —O—CO—$R^5$ in which $R^5$ denotes straight-chain or branched alkyl having up to 4 carbon atoms, $R^1$ and $R^2$ are identical or different and represent hydrogen, amino or represent straight-chain or branched alkyl, alkoxy or alkylamino having in each case up to 6 carbon atoms, $R^3$ and $R^4$ are identical or different and represent straight-chain or branched alkyl or acyl having in each case up to 4 carbon atoms, and salts thereof, with the exception of 3,5-diacetyl-2,4,6-trimethyl-4H-pyran, 3,5-diethoxycarbonyl-2,6-dimethyl-4-phenyl-4H-pyran and 3,5-diethoxycarbonyl-2,4,6-trimethyl-4H-pyran.

Particular preference is given to compounds of the general formula (I) in which

A represents cyclopropyl, cyclohexyl or represents straight-chain or branched alkyl having up to 4 carbon atoms, or represents naphthyl or phenyl which are optionally substituted up to 3 times by identical or different substituents consisting of nitro, cyano, fluoro, chloro, bromo, iodo, phenyl, naphthyl, carboxyl, cyclopropyl, cyclopentyl, cyclohexyl, trifluoromethyl, or by straight-chain or branched alkyl, alkoxycarbonyl, alkylthio or alkoxy having in each case up to 4 carbon atoms, or by a group of the formula —O—CO—$R^5$ in which $R^5$ denotes straight-chain or branched alkyl having up to 4 carbon atoms, $R^1$ and $R^2$ are identical or different and represent hydrogen, amino or represent straight-chain or branched alkyl, alkoxy or alkylamino having in each case up to 4 carbon atoms, $R^3$ and $R^4$ are identical or different and represent straight-chain or branched alkyl or acyl having in each case up to 4 carbon atoms, and salts thereof, with the exception of 3,5-diacetyl-2,4,6-trimethyl-4H-pyran, 3,5-diethoxycarbonyl-2,6-dimethyl-4-phenyl-4H-pyran and 3,5-diethoxycarbonyl-2,4,6-trimethyl-4H-pyran.

Moreover, a process has been found for the preparation of the compounds of the general formula (I) according to the invention, characterized in that

[A] aldehydes of the general formula (II)

$$A\text{—CHO} \qquad (II)$$

in which

A has the meaning given above are reacted with compounds of the general formula (III)

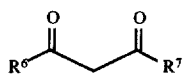 (III)

in which

R⁶ embraces the meanings of R¹ and R² given above in each case and

R⁷ embraces the meanings of R³ and R⁴ given above, or

[B] ylidene compounds of the general formula (IV)

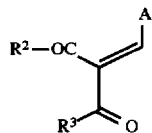 (IV)

in which

A, R² and R³ have the meanings given above, are reacted with compounds of the general formula (IIIa) or (IIIb)

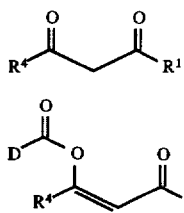 (IIIa)

(IIIb)

in which

R¹ and R⁴ have the meanings given above and

D together with the CO group, forms an electron-attracting, activated radical, with D representing for example hydrogen, trifluoromethyl, phenyl or $C_1$–$C_4$-alkyl, preferably methyl, in inert solvents in the presence of auxiliaries and/or in the presence of a dehydrating agent, and, in the case of the compounds of the general formula (I) in which R¹/R² represent amino and/or alkylamino, the corresponding acids are first of all prepared by hydrolysis from the esters, are converted into the carbonyl chlorides by transesterification, for example with thionyl chloride, and in a final step are reacted with ammonia or alkylamines.

The processes according to the invention can be illustrated by way of example using the following formula scheme:

1)
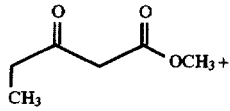

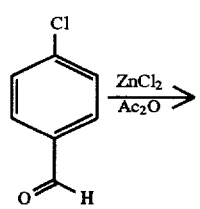

2)

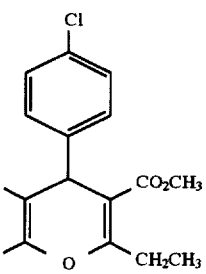

3)

4)

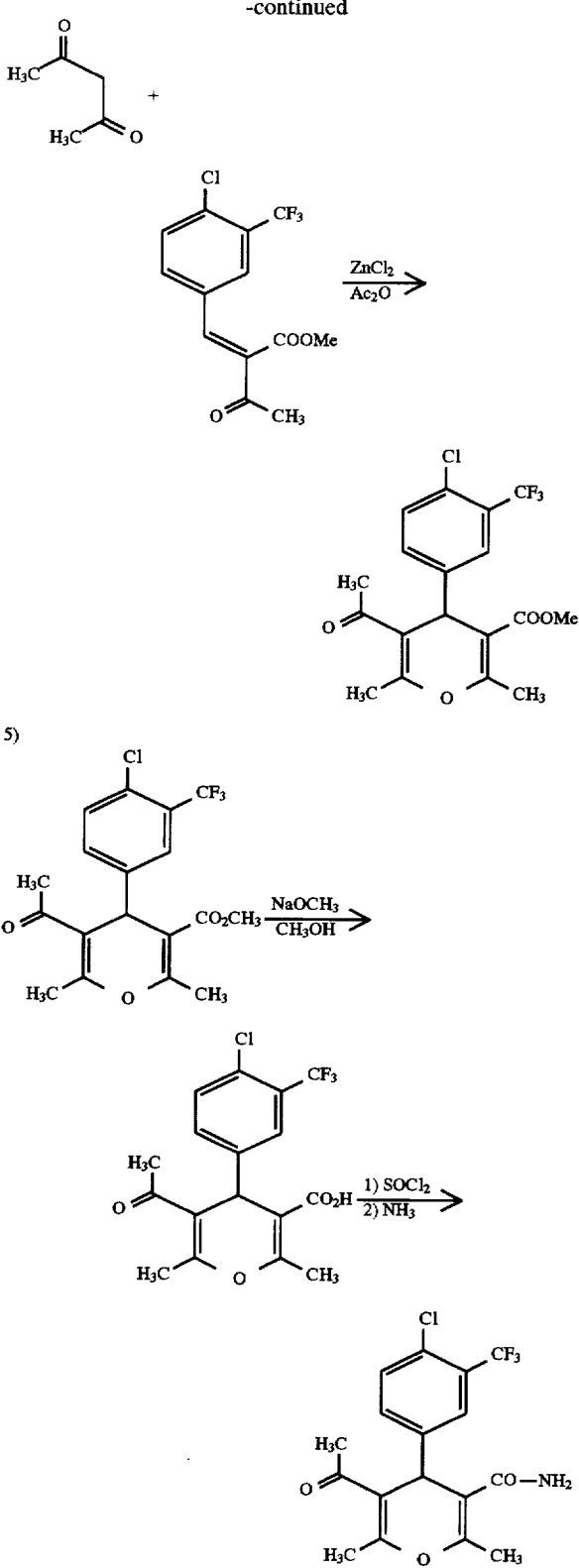

Suitable solvents are all inert organic solvents which do not change under the reaction conditions. These include, preferably, ethers such as diethyl ether, dioxane, tetrahydrofuran, glycol dimethyl ether or diethylene glycol dimethyl ether, ethyl acetate, or acetonitrile, or amides such as hexamethyl phosphoric triamide or dimethylformamide, or halogenated hydrocarbons such as methylene chloride, carbon tetrachloride or hydrocarbons such as benzene or toluene, or pyridine, or carboxylic acids such as AcOH or $CF_3COOH$. It is likewise possible to use mixtures of the solvents mentioned. Glacial acetic acid is preferred.

Suitable dehydrating agents are acid anhydrides and acid chlorides, such as acetic anhydride ($Ac_2O$), acetyl chloride (AcCl), $POCl_3$, $SOCl_2$, $SO_2Cl_2$ or molecular sieves. $Ac_2O$ is preferred. The water of reaction can also be removed azeotropically.

If enol acetates are incorporated by stirring, no dehydrating agent is necessary.

Examples of suitable auxiliaries are $TiCl_4$, $SnCl_4$, $BF_3\times OEt_2$, $Zn(OAc)_2$, $LiClO_4$ or zinc chloride. Zinc chloride is preferred.

The auxiliary is employed in a quantity of from 0.1 mol to 5 mol, preferably from 1 mol to 2 mol, based in each case on 1 mol of the compounds of the general formulae (II) and (IV).

The process is generally carried out in a temperature range from 0C to 150° C., preferably from 40° C. to 80° C.

The reactions can be carried out under atmospheric pressure, but also under elevated or reduced pressure (e.g. from 0.5 to 3 bar). They are generally carried out under atmospheric pressure.

The compounds of the general formulae (II), (III), (IIIa), (IIIb) and (IV) are known per se or can be prepared by customary methods.

Enantiomerically pure forms are obtained, for example, by using a customary method to separate diastereomer mixtures of the compounds of the genera formula (I) in which $R^1$ represents an optically active ester radical, then either subjecting the diastereomers directly to transesterification, or first preparing the chiral carboxylic acids and then preparing the enantiomerically pure compounds by esterification.

The diastereomers are generally separated either by fractional crystallization, by column chromatography or by Craig partition. The decision as to which process is optimal must be decided from case to case; in some cases it is also expedient to use combinations of the individual methods.

Separation by crystallization or Craig partition, or a combination of both methods, is particularly suitable.

The enantiomerically pure compounds are also obtainable by chromatography of the racemic esters on chiral phases.

The invention also relates to the use of the known compounds 3,5-diacetyl-2,4,6-trimethyl-4H-pyran, 3,5-diethoxycarbonyl-2,6-dimethyl-4-phenyl-4H-pyran and 3,5-diethoxycarbonyl-2-4,6-trimethyl-4H-pyran and of the compounds according to the invention as medicaments, especially as cerebrally active medicaments.

The known compounds and the compounds according to the invention of the general formula (I) display an unforeseeable, valuable spectrum of pharmacological action.

They are modulators having selectivity for calcium-dependent and charybdotoxin-sensitive potassium channels (IK(Ca) channels), in particular of the central nervous system.

On account of their pharmacological properties they can be employed for the preparation of medicaments, especially medicaments for the treatment of degenerative CNS disorders, for example in the case of occurrence of dementias such as multiinfarct dementia (MID), primary degenerative dementia (PDD), presenile and senile dementia in Alzheimer's disease, HIV dementia and other forms of dementia. They are additionally suitable for the treatment of Parkinson's disease or amyotrophic lateral sclerosis, and also multiple sclerosis.

The active compounds are additionally suitable for the treatment of brain function disorders in old age, of organic brain syndrome (OBS) and of age-related memory disorders (age-associated memory impairment, AAMI).

They are suitable for the prophylaxis and treatment and for the control of the sequelae of cerebral circulatory disorders such as cerebral ischaemias, strokes, craniocerebral traumata and of subarachnoid haemorrhages.

They are useful for the treatment of depressions and psychoses, e.g. schizophrenia. They are additionally suitable for the treatment of disorders of neuroendocrine secretion and of neurotransmitter secretion and health disorders connected therewith, such as mania, alcoholism, drug abuse, dependence or abnormal eating behaviour. Other areas of application are the treatment of migraine, sleep disorders and neuropathies. They are, moreover, suitable as analgesics.

The active compounds are suitable, furthermore, for the treatment of disorders of the immune system, in particular of T-lymphocyte proliferation, and for influencing the smooth musculature, in particular of the uterus, urinary bladder and bronchial tract, and for the treatment of diseases connected therewith, for example asthma and urinary incontinence, and for the treatment of high blood pressure, arrhythmia, angina, diabetes and sickle-cell anaemia, cancer, restenosis, chronic obstructive pulmonary disease and edema.

The present invention also includes pharmaceutical preparations which, in addition to inert, non-toxic, pharmaceutically appropriate auxiliaries and excipients, contain one or more compounds of the general formula (I), or which consist of one or more active compounds of the formula (I), and processes for the production of these preparations.

The active compounds of the formula (I) should be present in these preparations in a concentration of from 0.1 to 99.5% by weight, preferably from 0.5 to 95% by weight of the overall mixture.

In addition to the active compounds of the formula (I), the pharmaceutical preparations can also comprise other pharmaceutical active compounds.

The abovementioned pharmaceutical preparations can be prepared in a customary manner by known methods, for example using the auxiliary(ies) or excipient(s).

In general, it has proved advantageous to administer the active compound or compounds of the formula (I) in total quantities of from about 0.01 to about 100 mg/kg, preferably in total quantities of from about 1 mg/kg to 50 mg/kg of body weight every 24 hours, if desired in the form of a plurality of individual doses, in order to achieve the desired result.

However, if appropriate, it may be advantageous to depart from the quantities mentioned, depending in fact on the nature and on the body weight of the subject treated, on the individual response to the medicament, on the nature and severity of the disorder, on the type of preparation and administration, and on the time or interval at which administration is made.

Rubidium efflux from $C_6$-BU1 glioma cells

The experiments were carried out with slight modifications in accordance with the method described by Tas et al. (Neurosci. Lett. 94, 279–284 (1988)), using rat $C_6$-BU1 glioma cells. Detection is performed by atomic absorption spectroscopy.

EXAMPLES

Example 1

Dimethyl 4-(4-chlorophenyl)-2,6-diethyl-4H-pyran-3,5-dicarboxylate

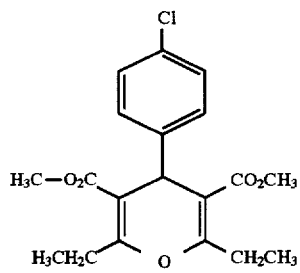

7.0 g (0.05 mol) of 4-chlorobenzaldehyde, 15.6 g (0.12 mol) of methyl 3-oxovalerate and 6.8 g (0.05 mol) of anhydrous zinc chloride are dissolved with stirring in a mixture of 9.3 g of glacial acetic acid and 10.4 g of acetic anhydride, and the solution is then left to stand at room temperature (20°–25° C.) for five weeks. The homogeneous solution is introduced into 100 g of ice and subjected to extraction with dichloromethane. The dichloromethane extracts are washed in succession with water, saturated sodium bicarbonate solution and water. The dichloromethane phase is dried over anhydrous sodium sulphate and filtered, the filtrate is evaporated in vacuo, and the residue (20.3 g) is chromatographed over 600 g of silica gel using toluene/ethyl acetate (10:1). 2.7 g of a uniform colourless oil are obtained which is freed from solvent residues by bulb-tube distillation (200° C./0.01 mbar).

$R_f$ (toluene/ethyl acetate=10:1): 0.52 $C_{19}H_{21}ClO_5$ Calc. C: 62.55%; H: 5.80% (364.8) Found C: 62.20%; H: 5.86% $^1$H-NMR (CDCl$_3$): δ=7.26–7.13 m (4, aromatic protons), 4.73 s (1, C4-H), 3.64 s (6, C3—COOCH$_3$ and C5—COOCH$_3$), 2.84 and 2.74 dddd, appears as a 12-line signal (4, C2—CH$_2$— and C6—CH$_2$)— and 1.90 ppm t (6, C2-CH$_2$-CH$_3$ and C6—CH$_2$—CH$_3$).

Example 2

3,5-Diacetyl-4-(4-chlorophenyl)-2,6-dimethyl-4H-pyran

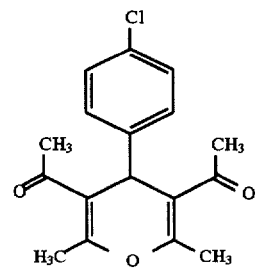

7.0 g (0.05 mol) of 4-chlorobenzaldehyde, 12.0 g (0.12 mol) of pentane-2,4-dione and 6.8 g (0.05 mol) of anhydrous zinc chloride are left to stand at room temperature for 3 weeks in a mixture of 8.9 ml of glacial acetic acid and 9.6 ml of acetic anhydride. The mixture is poured onto ice and subjected to extraction with dichloromethane. The organic extracts are washed in succession with saturated sodium bicarbonate solution and water, clarified over anhydrous sodium sulphate and filtered. Evaporation of the filtrate in vacuo yields 13.3 g of oil.

The crude product obtained from two identical batches is subjected to flash chromatography on silica gel with toluene/ethyl acetate (ascending gradient) and gives 9.6 g of a mixture of 2-acetyl-4-(4-chlorophenyl)-buten-2-one and 3,5-diacetyl-4-(4-chlorophenyl)-2,6-dimethyl-4H-pyran. Rechromatography over 700 g of silica gel using toluene and toluene/ethyl acetate=20:1 gives 4.1 g of uniform product.

m.p.: 86°–88° C. (cap.) (from dichloromethane/petroleum ether). $R_f$: 0.20 (toluene/ethyl acetate=10:1). $C_{17}H_{17}ClO_3$ Calc. C: 67.00%; H: 5.62% (304.8) Found C: 66.9%; H: 5.77% $^1$H-NMR (CDCl$_3$): δ=7.27–7.15 m (4, aromatic protons), 4.88 s (1, C4-H), 2.32 s (6, C3—COOCH$_3$ and C5—COOCH$_3$), and 2.21 ppm s (C2—CH$_3$ and C6—CH$_3$).

Example 3

Dimethyl 4-(4-chlorophenyl)-2,6-dimethyl-4H-pyran-dicarboxylate

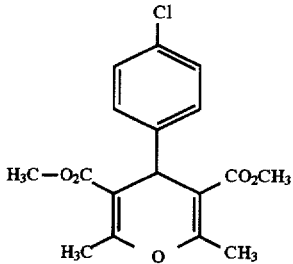

a) 13.9 g (0.12 mol) of methyl acetoacetate and 7.0 g (0.05 mol) of 4-chlorobenzaldehyde are introduced with stirring at 25° C. into a mixture of 9.6 ml of acetic anhydride and 6.8 g (0.05 mol) of anhydrous zinc chloride. With a temperature rise (to about 60° C.) a pale yellow solution is obtained which is heated for 8 h at 60°–65° C. 3 times. The reaction mixture is worked up by introducing it into 200 ml of ice water and subjecting the mixture to extraction with dichloromethane. The organic phase is washed in succession with water, saturated sodium bicarbonate solution and again with water, clarified over anhydrous sodium sulphate and filtered, and the filtrate is evaporated in vacuo. The residue (18.8 g) is chromatographed over silica gel (1650 g) with toluene/ethyl acetate=25:1, and yields 9.8 g (58%) of uniform pyran and 1.2 g of a mixture comprising equal parts of pyran and methyl 2-acetyl-3-(4-chlorophenyl)acrylate. Crystallization of the main fraction from petroleum ether/diethyl ether yields colourless crystals of m.p. 85°–86° C.

b) The title compound can be prepared analogously by reacting 17.4 g (0.11 mol) of methyl 3-acetoxycrotonate, 6.8 g of zinc chloride and 7 g (0.05 mol) of 4-chlorobenzaldehyde. After aqueous work-up, 14.9 g of crude product are obtained which is separated using silica gel and yields 10.5 g of uniform pyran.

$R_f$ (toluene/ethyl acetate=10:1): 0.41 $C_{17}H_{17}ClO_5$ Calc. C: 60.63%; H: 5.09% (336.8) Found C: 60.6%; H: 5.20% $^1$H-NMR (CDCl$_3$): δ=7.22–7.14 m (4, aromatic protons), 4.74 s (1, C4-H), 3.64 s (6, C3—COOCH$_3$ and C5—COOCH$_3$), and 2.36 ppm s (6, C2—CH$_3$ and C6—CH$_3$).

Example 4

Methyl ethyl 4-(4-chlorophenyl)-2,6-dimethyl-4H-pyran-dicarboxylate

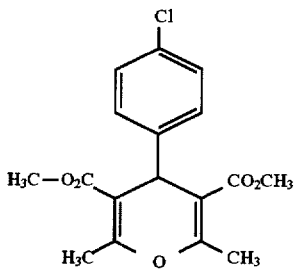

A mixture of 9.5 g (0.04 mol) of methyl 2-acetyl-3-(4-chlorophenyl)acrylate, 5.7 g (0.044 mol) of ethyl acetoacetate, 5.4 g (0.04 mol) of anhydrous zinc chloride and 7.5 ml of acetic anhydride is stirred for 8 h at 60°–65° C. 3 times. 4.0 ml of glacial acetic acid are added to the mixture, and stirring for 8 h at 60°–65° C. 3 times is repeated. After working up as described above, the crude product (15.9 g) is chromatographed over 2000 g of silica gel using toluene. 5.3 g (30%) of crystalline pyran are obtained. m.p.: 67°–69° C. (from petroleum ether).

$R_f$ (toluene/ethyl acetate=10:1): 0.53 $^1$H-NMR (CDCl$_3$): δ=7.22–7.14 m (4, aromatic protons), 4.73 s (1, C4-H), 4.09 2 qu (2, C3—COOCH$_2$—), 3.64 s (3, C5—COOCH$_3$), 2.36 s (6, C2—CH$_3$ and C6—CH$_3$) and 1.20 ppm t (3, C3—COOCH$_2$—CH$_3$).

Example 5

Methyl 5-acetyl-2,6-dimethyl-4-(4-chloro-3-trifluoromethyl)-4H-pyran-3-carboxylate

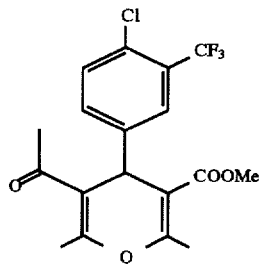

10 g (32.6 mmol) of methyl 2-acetyl-3-(4-chloro-3-trifluoromethylphenyl) acrylate and 10 g (97.8 mmol) of 2,4-pentanedione are stirred with 8.4 g of ZnCl$_2$ in 20 ml of acetic anhydride at 60° C. for 3 hours. After aqueous work-up and chromatography, 2.83 g of the title compound are obtained.

Melting point: 96° C. (petroleum ether) NMR (CDCl$_3$): 2.20 (s,3H), 2.36 (s,6H), 3.69 (s,3H), 4.82 (s,1H), 7.48 (m,2H), 7.51 (s,1H).

$C_{18}H_{18}O_4F_3Cl$ (388.77): Calc.: C: 55.61% H 4.15% O: 16.46% Found: C: 55.55% H 4.17% O: 16.32%

In addition, Example 5 is obtained as a by-product of the synthesis of Example 32.

The compounds listed in Tables I and 2 are prepared in analogy to the above Examples 1–5:

TABLE 1

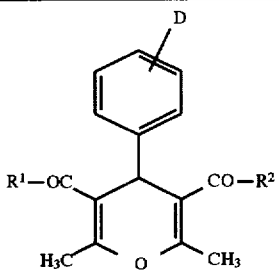

| Ex. No. | m.p. (°C.) (cap.) | $R_f$ (solv.) | $R^1$ | $R^2$ | D |
|---|---|---|---|---|---|
| 6 | 74–5 | 0.44 (A) | —OC$_2$H$_5$ | —OC$_2$H$_5$ | H |
| 7 | 84–5 | 0.44 (A) | —OC$_2$H$_5$ | —OC$_2$H$_5$ | 4-OCH$_3$ |
| 8 | 89 | 0.45 (A) | —OC$_2$H$_5$ | —OC$_2$H$_5$ | 3-NO$_2$ |
| 9 | 80 | 0.42 (A) | —OC$_2$H$_5$ | —OC$_2$H$_5$ | 2-OCH$_3$ |
| 10 | 99 | 0.49 (A) | —OC$_2$H$_5$ | —OC$_2$H$_5$ | 4-SCH$_3$ |
| 11 | 90 | 0.36 (A) | —OCH$_3$ | —OCH$_3$ | 2-OCH$_3$ |
| 12 | 106 | 0.43 (A) | —OC$_2$H$_5$ | —OC$_2$H$_5$ | 4-OH |
| 13 | 103–4 | 0.50 (A) | —OCH$_3$ | —OCH$_3$ | 3,4-Cl$_2$ |
| 14 | 81–2 | 0.62 (B) | —OCH$_3$ | —OCH$_3$ | 3-CH$_3$ |
| 15 | 64–5 | 0.46 (A) | —OC$_2$H$_5$ | —OC$_2$H$_5$ | 4-Cl |
| 16 | oil 200/0.01 mbar | 0.33 (A) | —OCH$_3$ | —OCH$_3$ | 3-COOCH$_3$ |
| 17 | 105–9 | 0.42 (A) | —OCH$_3$ | —OCH$_3$ | 4-C$_6$H$_5$ |
| 18 | 122–6 | 0.46 (A) | —OCH$_3$ | —OCH$_3$ | 2-CH$_3$ |
| 19 | 80–3 | 0.35 (A) | —OCH$_3$ | —OCH$_3$ | 3-Cl |
| 20 | 62–4 | 0.41 (A) | —OCH$_3$ | —OCH$_3$ | H |
| 21 | 73–6 | 0.41 (A) | —OCH$_3$ | —OCH$_3$ | 4-F |
| 22 | 68–9 | 0.47 (A) | —OCH$_3$ | —OCH$_3$ | 3,4-F$_2$ |
| 23 | 85–6 | 0.30 (A) | —OCH$_3$ | —OCH$_3$ | 3-OCOCH$_3$ |
| 24 | 45–6 | 0.51 (A) | —O-n-C$_3$H$_7$ | —O-n-C$_3$H$_7$ | 4-Cl |
| 25 | 51–3 | 0.56 (A) | —O-n-C$_4$H$_9$ | —O-n-C$_4$H$_9$ | 4-Cl |
| 26 | 88–9 | 0.46 (A) | —OC$_2$H$_5$ | —OC$_2$H$_5$ | 2,3-Cl$_2$ |
| 27 | 98–100 | 0.40 (A) | —OCH$_3$ | OCH$_3$ | 2,3-Cl$_2$ |
| 28 | 67–9 | 0.53 (A) | —OCH$_3$ | —OC$_2$H$_5$ | 4-Cl |
| 29 | 105–9 | 0.40 (A) | —OCH$_3$ | —OCH$_3$ | 4-C$_6$H$_5$ |
| 30 | 90 | 0.64 A) | —OCH$_3$ | —OCH$_3$ | 4-CF$_3$ |
| 31 | 69 | 0.55 (A) | —OCH$_3$ | —OCH$_3$ | 3-CF$_3$ |
| 32 | 81.5 | 0.41 (A) | —CH$_3$ | —OCH$_3$ | 3-CF$_3$ |
| 33 | 120 | 0.53 (A) | —OCH$_3$ | —OCH$_3$ | 4-Cl, 3-CF$_3$ |
| 34 | 96 | 0.41 (A) | —CH$_3$ | —OCH$_3$ | 4-Cl, 3-CF$_3$ |
| 35 | 86 | 0.29 (A) | —CH$_3$ | —CH$_3$ | 4-Cl, 3-CF$_3$ |
| 36 | 106 | 0.32 (A) | —CH$_3$ | —CH$_3$ | (3,4.5)-F$_3$ |
| 37 | 50 | 0.27 (A) | —CH$_3$ | —CH$_3$ | 4-CF$_3$ |
| 38 | 91 | 0.31 (A) | —CH$_3$ | —CH$_3$ | 3-CF$_3$ |

TABLE 2

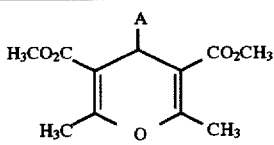

| Ex. No. | A | m.p. (°C.) | $R_f$ (solv.) |
|---|---|---|---|
| 39 | cyclohexyl | 68–70 | 0.49 (A) |
| 40 | α-Naphthyl | 127–9 | 0.40 (A) |

$R_f$ solv.: A: Toluene/ethyl acetate = 10:1

Example 41

5-Acetyl-4-(4-chloro-3-trifluoromethylphenyl)-2,6-dimethyl-4H-pyran-3-carboximide

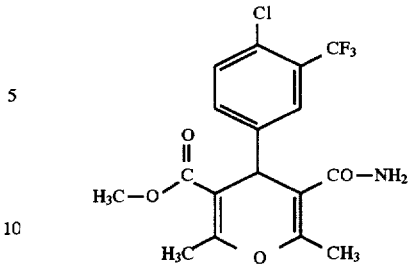

Preliminary stage a)

1.01 g (2.57 mmol) are dissolved in 10 ml of THF, 10 ml of MeOH and 10 ml of 1N NaOH are added, and the mixture is stirred at RT overnight. The solvent is then removed by distillation and the residue is partitioned between water and Et$_2$O. The aqueous phase is adjusted to a pH of 5 and the precipitate which forms is filtered off with suction and washed. 432 mg (45% of theory) are obtained of a colourless powder which has sufficient purity for subsequent reactions.

Preliminary stage b)

1 g of the above acid is dissolved in 10 ml of SOCl$_2$ and the solution is refluxed for 1.5 h. The reagent is then removed by distillation and the residue is taken up in 50 ml of THF.

10 ml of 25% strength ammonia water are added, with cooling, and the mixture is stirred at RT for 30 min. It is then concentrated and the residue is partitioned between ethyl acetate (AcOEt) and H$_2$O. Following extraction (AcOEt), drying (MgSO$_4$) and concentration are carried out.

The crude product is purified by chromatography on silica gel (petroleum ether/AcOH, gradient). 319 mg, 31%, of a pale brown powder are obtained.

Melting point: 129° C. $R_f$=0.65 NMR: (CDCl$_3$ 200 MHz): 2.18 (s, 3H); 2.24 (s, 3H); 2.35 (s, 3H); 4.82 (s, 1H); 5.10–5.40 (m, br, 2H) and 7.31–7.52 ppm (m, 3H).

Examples 42 and 43

4-(4-chlorophenyl)-2,6-dimethyl-4H-pyran-3,5-dicarboxylic acid 3-methyl ester 5-N-methylamide and N,N'-dimethyl-4-(4-chlorophenyl)-2,6-dimethyl-4H-pyran-3,5-dicarboxamide (42)

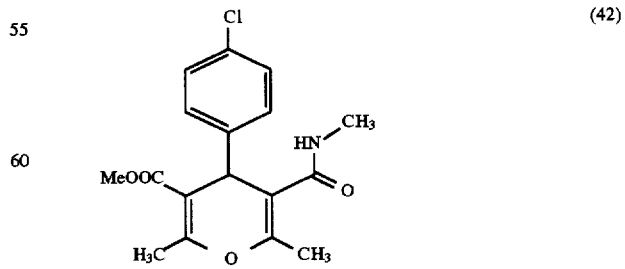

and

-continued

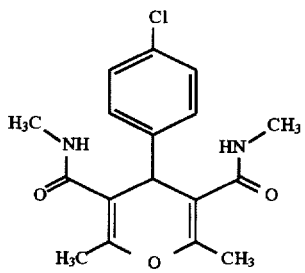

(43)

2.0 ml of trimethylaluminium solution (5 m in n-hexane) are introduced slowly under argon at 5° C. into a suspension of 1.35 g (20 mmol) of methylammonium chloride in 20 ml of absolute toluene. The temperature is allowed to rise to 25° C., the mixture is stirred for 1 to 2 hours until the evolution of gas has reached an end, and a clear solution is obtained (1 m solution of the reagent).

2.0 g (6 mmol) of dimethyl 4-(4-chlorophenyl)-2,6-dimethyl-4H-pyran-3,5-dicarboxylate in 60 ml of absolute toluene are added dropwise at 25° C. under argon to the resulting solution of the reagent (20 mmol). After heating at 80° C. for 12 hours (TLC monitoring of the degree of conversion), the mixture is cooled to 25° C. and acidified carefully with 5% strength aqueous hydrochloric acid. The organic phase is separated off and the aqueous phase is subjected to extraction 3 times with ethyl acetate. The combined organic phases are washed with water until neutral, dried over sodium sulphate and filtered, and the filtrate is concentrated in vacuo. The crude product (1.5 g) is separated over silica gel using toluene/ethyl acetate/methanol (gradient) and yields 0.1 g of starting material, 0.7 g of the mono-N-methylamide and 0.7 g of the bis-N-methylamide.

4-(4-chlorophenyl)-2,6-dimethyl-4H-pyran-3,5-dicarboxylic acid 3-methyl ester 5-N-methylamide (Example 42)

Melting point: 163°–165° C. (cap.) (from dichloromethane/petroleum ether), R$_f$ (toluene/ethyl acetate 3:1): 0.18 C$_{17}$H$_{18}$ClNO$_4$ Calc. C 60.81% H 5.40% N 4.17% (335.8) Found 60.6, 5.36, 4.23 NMR (CDCl$_3$): 2.20 (s, 3H), 2.30 (s, 3H), 2.70 (d, 6H), 3.60 (s, 3H), 4.55 (s, 1H), 5.20 (br, s, 1H) and 7.20–7.30 ppm (m, 4H).

N,N'-dimethyl-4-(4-chlorophenyl)-2,6-dimethyl-4H-pyran-3,5-dicarboxamide (Example 43)

Melting point: 256°–259° C. (cap.) (from ethyl acetate), R$_f$ (ethyl acetate): 0.13 C$_{17}$H$_{18}$ClNO$_4$ Calc. C 60.9% H 5.70% N 8.66 % (334.8) Found: 60.99, 5.72, 8.37 NMR (CDCl$_3$): 2.13 (s, 6H), 2.70 (d, 6H), 4.50 (s, 1H), 5.30 (br, s, 2H), and 7.20–7.35 ppm (m, 4H).

The Examples specified in the table are prepared in analogy to the abovementioned procedures of Examples 41 to 43.

TABLE 3

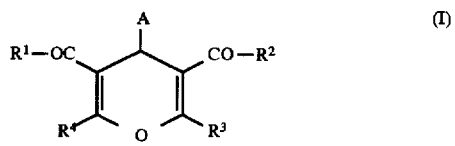

| Ex. No. | A | R$^2$ | m.p. | R$_f$ |
|---|---|---|---|---|
| 44 | F-phenyl (2,6-difluoro-4-iodo) | NH$_2$ | >220° | 0.33 (AcOEt) |
| 45 | | OCH$_3$ | 133° | 0.74 (AcOEt) |
| 46 | 2-Cl, 5-CF$_3$-phenyl | NH$_2$ | >220° | 0.35 (AcOEt) |
| 41 | | OCH$_3$ | 154° | 0.89 (AcOEt) |
| 47 | 3-CF$_3$-phenyl | NH$_2$ | 210° C. | 0.55 (AcOEt) |
| 48 | | OCH$_3$ | 142.5 | 0.94 (AcOEt) |
| 49 | 3,5-difluorophenyl | NH$_2$ | >220° | 0.39 (AcOEt) |
| 50 | | OCH$_3$ | 167.5° | 0.8 (AcOEt) |

We claim:
1. A substituted 4H-pyran of the formula (I):

(I)

$$R^1-OC \underset{R^4 \quad O \quad R^3}{\overset{A}{\diagdown}} CO-R^2$$

in which

A represents cycloalkyl having 3 to 6 carbon atoms; or represents straight-chain or branched alkyl having up to 8 carbon atoms; or represents aryl having 6 to 10 carbon atoms or pyridyl, each of which is optionally substituted 1 to 3 times by identical or different substituents selected from the group consisting of nitro, hydroxyl, carboxyl, cyano, aryl having 6 to 10 carbon atoms, halogen, cycloalkyl having 3 to 6 carbon atoms, trifluoromethyl, straight-chain or branched alkyl, alkoxycarbonyl, alkylthio or alkoxy having in each case up to 6 carbon atoms, and radicals of the formula —O—CO—R$^5$, in which R$^5$ represents straight-chain or branched alkyl having up to 6 carbon atoms;

$R^1$ and $R^2$ are identical or different and represent hydrogen, amino, or straight-chain or branched alkyl, alkoxy or alkylamino having in each case up to 8 carbon atoms; and $R^3$ and $R^4$ are identical or different and represent straight-chain or branched alkyl or acyl having in each case up to 6 carbon atoms;

or a physiologically acceptable salt thereof;

with the exception of 3,5-diacetyl-2,4,6-trimethyl-4H-pyran; 3,5-diethoxycarbonyl-2,6-dimethyl-4-phenyl-4H-pyran; and 3,5-diethoxycarbonyl-2,4,6-trimethyl-4H-pyran.

2. A substituted 4H-pyran of the formula (I) according to claim 1, in which

A represents cyclopropyl, cyclobutyl, cyclopentyl or cyclohexyl; or represents straight-chain or branched alkyl having up to 6 carbon atoms; or represents phenyl, naphthyl or pyridyl, each of which is optionally substituted 1 to 3 times by identical or different substituents selected from the group consisting of nitro, cyano, fluoro, chloro, bromo, iodo, phenyl, naphthyl, trifluoromethyl, hydroxyl, carboxyl, cyclopropyl, cyclopentyl, cyclohexyl, straight-chain or branched alkyl, alkoxycarbonyl, alkylthio or alkoxy having in each case up to 4 carbon atoms, and radicals of the formula —O—CO—$R^5$, in which $R^5$ represents straight-chain or branched alkyl having up to 4 carbon atoms;

$R^1$ and $R^2$ are identical or different and represent hydrogen, amino, or straight-chain or branched alkyl, alkoxy or alkylamino having in each case up to 6 carbon atoms; and $R^3$ and $R^4$ are identical or different and represent straight-chain or branched alkyl having up to 4 carbon atoms;

or a physiologically acceptable salt thereof;

with the exception of 3,5-diacetyl-2,4,6-trimethyl-4H-pyran; 3,5-diethoxycarbonyl-2,6-dimethyl-4-phenyl-4H-pyran; and 3,5-diethoxycarbonyl-2,4,6-trimethyl-4H-pyran.

3. A substituted 4H-pyran of the formula (I) according to claim 1, in which

A represents cyclopropyl or cyclohexyl; or represents straight-chain or branched alkyl having up to 4 carbon atoms; or represents phenyl or naphthyl, each of which is optionally substituted 1 to 3 times by identical or different substituents selected from the group consisting of nitro, cyano, fluoro, chloro, bromo, iodo, phenyl, naphthyl, hydroxyl, carboxyl, cyclopropyl, cyclopentyl, cyclohexyl, trifluoromethyl, straight-chain or branched alkyl, alkoxycarbonyl, alkylthio or alkoxy having in each case up to 4 carbon atoms, and radicals of the formula —O—CO—$R^5$, in which $R^5$ represents straight-chain or branched alkyl having up to 4 carbon atoms;

$R^1$ and $R^2$ are identical or different and represent hydrogen, amino, or straight-chain or branched alkyl, alkoxy or alkylamino having in each case up to 4 carbon atoms; and $R^3$ and $R^4$ are identical or different and represent straight-chain or branched alkyl having up to 4 carbon atoms;

or a physiologically acceptable salt thereof;

with the exception of 3,5-diacetyl-2,4,6-trimethyl-4H-pyran; 3,5-diethoxycarbonyl-2,6-dimethyl-4-phenyl-4H-pyran; and 3,5-diethoxycarbonyl-2,4,6-trimethyl-4H-pyran.

4. A composition for treating a disorder of the central nervous system comprising a pharmaceutically acceptable carrier and an effective amount therefor of a substituted 4H-pyran of the formula (I):

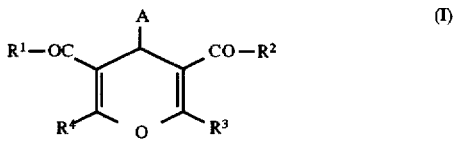

in which

A represents cycloalkyl having 3 to 6 carbon atoms; or represents straight-chain or branched alkyl having up to 8 carbon atoms; or represents aryl having 6 to 10 carbon atoms or pyridyl, each of which is optionally substituted 1 to 3 times by identical or different substituents selected from the group consisting of nitro, hydroxyl, carboxyl, cyano, aryl having 6 to 10 carbon atoms, halogen, cycloalkyl having 3 to 6 carbon atoms, trifluoromethyl, straight-chain or branched alkyl, alkoxycarbonyl, alkylthio or alkoxy having in each case up to 6 carbon atoms, and radicals of the formula —O—CO—$R^5$, in which $R^5$ represents straight-chain or branched alkyl having up to 6 carbon atoms;

$R^1$ and $R^2$ are identical or different and represent hydrogen, amino, or straight-chain or branched alkyl, alkoxy or alkylamino having in each case up to 8 carbon atoms; and $R^3$ and $R^4$ are identical or different and represent straight-chain or branched alkyl or acyl having in each case up to 6 carbon atoms;

or a physiologically acceptable salt thereof.

5. A composition according to claim 4, wherein in the substituted 4H-pyran of the formula (I), A represents cyclopropyl, cyclobutyl, cyclopentyl or cyclohexyl; or represents straight-chain or branched alkyl having up to 6 carbon atoms; or represents phenyl, naphthyl or pyridyl, each of which is optionally substituted 1 to 3 times by identical or different substituents selected from the group consisting of nitro, cyano, fluoro, chloro, bromo, iodo, phenyl, naphthyl, trifluoromethyl, hydroxyl, carboxyl, cyclopropyl, cyclopentyl, cyclohexyl, straight-chain or branched alkyl, alkoxycarbonyl, alkylthio or alkoxy having in each case up to 4 carbon atoms, and radicals of the formula —O—CO—$R^5$, in which $R^5$ represents straight-chain or branched alkyl having up to 4 carbon atoms;

$R^1$ and $R^2$ are identical or different and represent hydrogen, amino, or straight-chain or branched alkyl, alkoxy or alkylamino having in each case up to 6 carbon atoms; and $R^3$ and $R^4$ are identical or different and represent straight-chain or branched alkyl having up to 4 carbon atoms;

or a physiologically acceptable salt thereof.

6. A method of treating a patient for a disorder of the central nervous system, said method comprising administering to said patient an effective amount therefor of a substituted 4H-pyran of the formula (I):

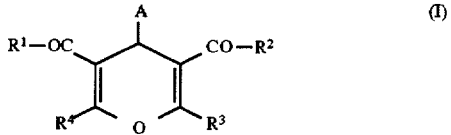

in which

A represents cycloalkyl having 3 to 6 carbon atoms; or represents straight-chain or branched alkyl having up to 8 carbon atoms; or represents aryl having 6 to 10 carbon atoms or pyridyl, each of which is optionally substituted 1 to 3 times by identical or different substituents selected from the group consisting of nitro, hydroxyl, carboxyl, cyano, aryl having 6 to 10 carbon atoms, halogen, cycloalkyl having 3 to 6 carbon atoms, trifluoromethyl, straight-chain or branched alkyl, alkoxycarbonyl, alkylthio or alkoxy having in each case up to 6 carbon atoms, and radicals of the formula $-O-CO-R^5$, in which $R^5$ represents straight-chain or branched alkyl having up to 6 carbon atoms;

$R^1$ and $R^2$ are identical or different and represent hydrogen, amino, or straight-chain or branched alkyl, alkoxy or alkylamino having in each case up to 8 carbon atoms; and $R^3$ and $R^4$ are identical or different and represent straight-chain or branched alkyl or acyl having in each case up to 6 carbon atoms; or a physiologically acceptable salt thereof.

7. A method according to claim 6, wherein in the substituted 4H-pyran of the formula (I), A represents cyclopropyl, cyclobutyl, cyclopentyl or cyclohexyl; or represents straight-chain or branched alkyl having up to 6 carbon atoms; or represents phenyl, naphthyl or pyridyl, each of which is optionally substituted 1 to 3 times by identical or different substituents selected from the group consisting of nitro, cyano, fluoro, chloro, bromo, iodo, phenyl, naphthyl, trifluoromethyl, hydroxyl, carboxyl, cyclopropyl, cyclopentyl, cyclohexyl, straight-chain or branched alkyl, alkoxycarbonyl, alkylthio or alkoxy having in each case up to 4 carbon atoms, and radicals of the formula $-O-CO-R^5$, in which $R^5$ represents straight-chain or branched alkyl having up to 4 carbon atoms;

$R^1$ and $R^2$ are identical or different and represent hydrogen, amino, or straight-chain or branched alkyl, alkoxy or alkylamino having in each case up to 6 carbon atoms; and $R^3$ and $R^4$ are identical or different and represent straight-chain or branched alkyl having up to 4 carbon atoms;

or a physiologically acceptable salt thereof.

8. A substituted 4H-pyran of the formula (I):

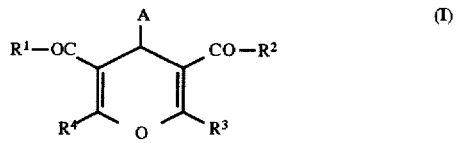

in which

A represents cycloalkyl having 3 to 6 carbon atoms; or represents aryl having 6 to 10 carbon atoms or pyridyl, each of which is optionally substituted 1 to 3 times by identical or different substituents selected from the group consisting of nitro, hydroxyl, carboxyl, cyano, aryl having 6 to 10 carbon atoms, halogen, cycloalkyl having 3 to 6 carbon atoms, trifluoromethyl, straight-chain or branched alkyl, alkoxycarbonyl, alkylthio or alkoxy having in each case up to 6 carbon atoms, and radicals of the formula $-O-CO-R^5$, in which $R^5$ represents straight-chain or branched alkyl having up to 6 carbon atoms;

$R^1$ and $R^2$ are different and represent hydrogen, amino, or straight-chain or branched alkyl, alkoxy or alkylamino having in each case up to 8 carbon atoms; or $R^1$ and $R^2$ are identical and represent hydrogen, amino, or straight-chain or branched alkylamino having up to 8 carbon atoms; and $R^3$ and $R^4$ are identical or different and represent straight-chain or branched alkyl or acyl having in each case up to 6 carbon atoms;

or a physiologically acceptable salt thereof.

9. A substituted 4H-pyran of the formula (I) according to claim 8, in which

A represents cyclopropyl, cyclobutyl, cyclopentyl or cyclohexyl; or represents phenyl, naphthyl or pyridyl, each of which is optionally substituted 1 to 3 times by identical or different substituents selected from the group consisting of nitro, cyano, fluoro, chloro, bromo, iodo, phenyl, naphthyl, trifluoromethyl, hydroxyl, carboxyl, cyclopropyl, cyclopentyl, cyclohexyl, straight-chain or branched alkyl, alkoxycarbonyl, alkylthio or alkoxy having in each case up to 4 carbon atoms, and radicals of the formula $-O-CO-R^5$, in which $R^5$ represents straight-chain or branched alkyl having up to 4 carbon atoms;

$R^1$ and $R^2$ are different and represent hydrogen, amino, or straight-chain or branched alkyl, alkoxy or alkylamino having in each case up to 6 carbon atoms; or $R^1$ and $R^2$ are identical and represent hydrogen, amino, or straight-chain or branched alkylamino having up to 6 carbon atoms; and $R^3$ and $R^4$ are identical or different and represent straight-chain or branched alkyl having up to 4 carbon atoms;

or a physiologically acceptable salt thereof.

10. A substituted 4H-pyran of the formula (I) according to claim 8, in which

A represents cyclopropyl or cyclohexyl; or represents phenyl or naphthyl, each of which is optionally substituted 1 to 3 times by identical or different substituents selected from the group consisting of nitro, cyano, fluoro, chloro, bromo, iodo, phenyl, naphthyl, hydroxyl, carboxyl, cyclopropyl, cyclopentyl, cyclohexyl, trifluoromethyl, straight-chain or branched alkyl, alkoxycarbonyl, alkylthio or alkoxy having in each case up to 4 carbon atoms, and radicals of the formula —O—CO—$R^5$, in which $R^5$ represents straight-chain or branched alkyl having up to 4 carbon atoms;

$R^1$ and $R^2$ are different and represent hydrogen, amino, or straight-chain or branched alkyl, alkoxy or alkylamino having in each case up to 4 carbon atoms; or $R^1$ and $R^2$ are identical and represent hydrogen, amino, or straight-chain or branched alkylamino having up to 4 carbon atoms; and $R^3$ and $R^4$ are identical or different and represent straight-chain or branched alkyl having up to 4 carbon atoms;

or a physiologically acceptable salt thereof.

11. A composition for treating a disorder of the central nervous system comprising a pharmaceutically acceptable carrier and an effective amount therefor of a substituted 4H-pyran of the formula (I) according to claim 8.

12. A method of treating a patient for a disorder of the central nervous system, said method comprising administering to said patient an effective amount therefor of a substituted 4H-pyran of the formula (I) according to claim 8.

13. A composition according to claim 4, wherein the substituted 4H-pyran is a member selected from the group consisting of 3,5-diacetyl-2,4,6-trimethyl-4H-pyran, 3,5-diethoxycarbonyl-2,6-dimethyl-4-phenyl-4H-pyran and 3,5-diethoxycarbonyl-2,4,6-trimethyl-4H-pyran.

14. The method according to claim 6, wherein the substituted 4H-pyran is a member selected from the group consisting of 3,5-diacetyl-2,4,6-trimethyl-4H-pyran, 3,5-diethoxycarbonyl-2,6-dimethyl-4-phenyl-4H-pyran and 3,5-diethoxycarbonyl-2,4,6-trimethyl-4H-pyran.

* * * * *